(12) United States Patent
Wilkinson et al.

(10) Patent No.: US 7,060,055 B2
(45) Date of Patent: *Jun. 13, 2006

(54) FORWARD SHIELDING SAFETY DEVICE

(75) Inventors: Bradley M. Wilkinson, North Haledon, NJ (US); Volker Niermann, Bound Brook, NJ (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 109 days.

This patent is subject to a terminal disclaimer.

(21) Appl. No.: 10/628,223

(22) Filed: Jul. 28, 2003

(65) Prior Publication Data

US 2004/0024370 A1 Feb. 5, 2004

Related U.S. Application Data

(63) Continuation of application No. 10/100,307, filed on Mar. 15, 2002, now Pat. No. 6,623,461.

(51) Int. Cl.
*A61M 5/00* (2006.01)
(52) U.S. Cl. ..................................... 604/263
(58) Field of Classification Search ................ 604/263, 604/197, 198, 177, 162, 110, 192
See application file for complete search history.

(56) References Cited

U.S. PATENT DOCUMENTS

| | | | |
|---|---|---|---|
| 3,595,230 A | 7/1971 | Suyeoka et al. |
| 4,326,519 A | 4/1982 | D'Alo et al. |
| 4,964,854 A | 10/1990 | Luther |
| 5,085,639 A | 2/1992 | Ryan |
| 5,088,982 A | 2/1992 | Ryan |
| 5,112,311 A | 5/1992 | Utterberg et al. |
| 5,120,320 A | 6/1992 | Fayngold |
| 5,154,699 A | 10/1992 | Ryan |
| 5,192,275 A | 3/1993 | Burns |
| 5,266,072 A | 11/1993 | Utterberg et al. |
| 5,290,264 A | 3/1994 | Utterberg |
| 5,312,359 A | 5/1994 | Wallace |
| 5,498,241 A | 3/1996 | Fabozzi |
| 5,562,636 A | 10/1996 | Utterberg |
| 5,562,637 A | 10/1996 | Utterberg |
| 5,573,512 A | 11/1996 | van den Haak |
| 5,738,665 A | 4/1998 | Caizza et al. |
| RE36,398 E | 11/1999 | Byrne et al. |
| RE36,447 E | 12/1999 | Byrne et al. |
| 5,997,507 A | 12/1999 | Dysarz |
| 6,165,157 A | 12/2000 | Dillon et al. |

FOREIGN PATENT DOCUMENTS

JP 8-206195 8/1996

*Primary Examiner*—Sharon Kennedy
(74) *Attorney, Agent, or Firm*—Mark J. Schildkraut; Mark Lindsey

(57) ABSTRACT

The present invention is directed to a shieldable blood collection set as well as a needle assembly for use therein. The needle assembly includes a needle cannula having a puncture tip at a distal end thereof and a hub which supports the needle cannula. A hollow outer shield co-axially surrounds a distal end of the hub and has an inner surface which is in cooperating engagement with an outer surface of the hub. The hub includes a first tab extending outwardly at a position which is exposed from the outer shield, and the outer shield includes a second tab. The first tab and the second tab are configured such that opposing forces applied against the tabs cause the outer shield to move from a retracted position in which the puncture tip of the needle cannula is exposed, to an extended position in which the outer shield covers the puncture tip.

15 Claims, 6 Drawing Sheets

FORWARD SHIELDING SAFETY DEVICE

RELATED APPLICATION

This application is a continuation of application Ser. No. 10/100,307 filed Mar. 15, 2002.

BACKGROUND OF THE INVENTION

1. Field of the Invention

The present invention relates to blood collection sets for safe and convenient handling of needles. More particularly, the present invention relates to a blood collection set including a needle assembly having a forward moving safety shield for protection from a used needle tip.

2. Description of Related Art

Disposable medical devices having piercing elements are typically used for administering a medication or withdrawing a fluid, such as blood collecting needles, fluid handling needles and assemblies thereof. Current medical practice requires that the fluid containers and needle assemblies used in such systems be inexpensive and readily disposable. Consequently, existing blood collection systems, for example, typically employ some form of durable, reusable holder on which detachable and disposable needles and fluid collection tubes may be mounted. A blood collection system of this nature can be assembled prior to use and then disassembled after usage. Thus, these blood collection systems allow repeated use of the relatively expensive holder upon replacement of the relatively inexpensive needle and/or fluid collection tube. In addition to reducing the cost of collecting blood specimens, these blood collection systems also help minimize the production of hazardous medical waste.

A blood collection set or intravenous (IV) infusion set typically includes a needle cannula having a proximal end, a pointed distal end and a lumen extending therebetween. The proximal end of the needle cannula is securely mounted in a plastic hub with a central passage that communicates with the lumen through the needle cannula. A thin flexible thermoplastic tube is connected to the hub and communicates with the lumen of the needle cannula. The end of the plastic tube remote from the needle cannula may include a fixture for connecting the needle cannula to a blood collection tube or some other receptacle. The specific construction of the fixture will depend upon the characteristics of the receptacle to which the fixture will be connected.

In order to reduce the risk of incurring an accidental needle-stick wound, protection of used needle tips becomes important. With concern about infection and transmission of diseases, methods and devices to enclose the used disposable needle have become very important and in great demand. For example, some needle assemblies commonly employ a safety shield that can be moved into shielding engagement with a used needle cannula without risking an accidental needle stick.

U.S. Pat. Nos. 5,085,639, 5,088,982 and 5,154,699 disclose safety winged needle devices for use with blood collection sets or infusion sets. The safety needle devices of these patents include an inner tube and an outer tube having cooperating surfaces in contact with each other, with the cooperating surfaces having mating grooves and ramps. By applying a force in opposing directions on the inner and outer tubes, the outer tube is forcibly moved along the ramps and into engagement with the grooves of the inner tube, thereby moving the outer tube, and therefore the outer shield, into a shielding position and locking the shield in place about the needle tip. The cooperating surfaces of such outer and inner tubes, however, provide a frictional engagement which requires much force to overcome. Moreover, maintaining an appropriate grip on the needle device to forcibly move the outer and inner tubes apart can be difficult due to the profile of the needle device.

U.S. Pat. No. 6,165,157 discloses a needle guard which includes a "thumb-knob" or protrusion on the outer guard to assist in manipulation of the outer guard by providing an abutment against which the thumb of the user can push in order to pull the needle and needle mount into the outer guard using only one hand. Retraction of the needle in this manner, however, requires the user to grip the flexible tube in the user's palm, which does not provide an effective gripping surface for maintaining the needle device in place during retraction, and may cause the flexible tube to be separated from the needle device during retraction.

Accordingly, a need exists for a needle assembly for use with a blood collection set which achieves secure and effective shielding of a used needle tip and which is simple and inexpensive to manufacture and easy to operate.

SUMMARY OF THE INVENTION

The present invention is directed to a shieldable blood collection set as well as a needle assembly for use in a blood collection set. The needle assembly includes a hub including an elongated tubular body having an outer surface, a proximal end, a distal end and a passageway extending therethrough. The hub further includes a first tab extending outwardly from the proximal end of the tubular body for engagement with a user's finger. The distal end of the hub supports a needle cannula, which includes a puncture tip at a distal end thereof. A hollow outer shield co-axially surrounds the distal end of the tubular body of the hub. The outer shield includes a housing having a proximal end, a distal end and a passageway extending therethrough, as well as a second tab extending outwardly from the housing for engagement with a user's thumb. The first tab extends from the tubular body of the hub at a position which is exposed from the proximal end of the outer shield, and the housing of the outer shield has an inner surface which is in cooperating engagement with the outer surface of the hub.

The first tab and the second tab are configured such that opposing forces applied against the first tab and the second tab cause the outer shield to move toward the distal end of the needle cannula from a retracted position in which the puncture tip of the needle cannula is exposed, to an extended position in which the outer shield covers the puncture tip of the needle cannula.

Desirably, the first tab extends from a bottom portion of the hub and the second tab extends from a top portion of the housing of the outer shield at a position adjacent the first tab. As such, the first and second tabs are configured for engagement with a user's finger and thumb, respectively, for activation and movement of the outer shield from the retracted position to the activated position.

In particularly desirable embodiments, the outer surface of the hub includes a series of grooves and ramps and the inner surface of the outer shield cooperates with the outer surface of the hub. Such corresponding grooves and ramps provide for frictional engagement between the outer shield and the hub, thereby preventing the outer shield from movement between the retracted position and the activated position until a force is exerted thereon.

The present invention further includes a blood collection set including a needle assembly as described, a fixture for connecting the blood collection set to a receptacle, and a flexible tube extending between the blood collection set and the needle assembly at the proximal end of the hub.

DETAILED DESCRIPTION

Figure 1:
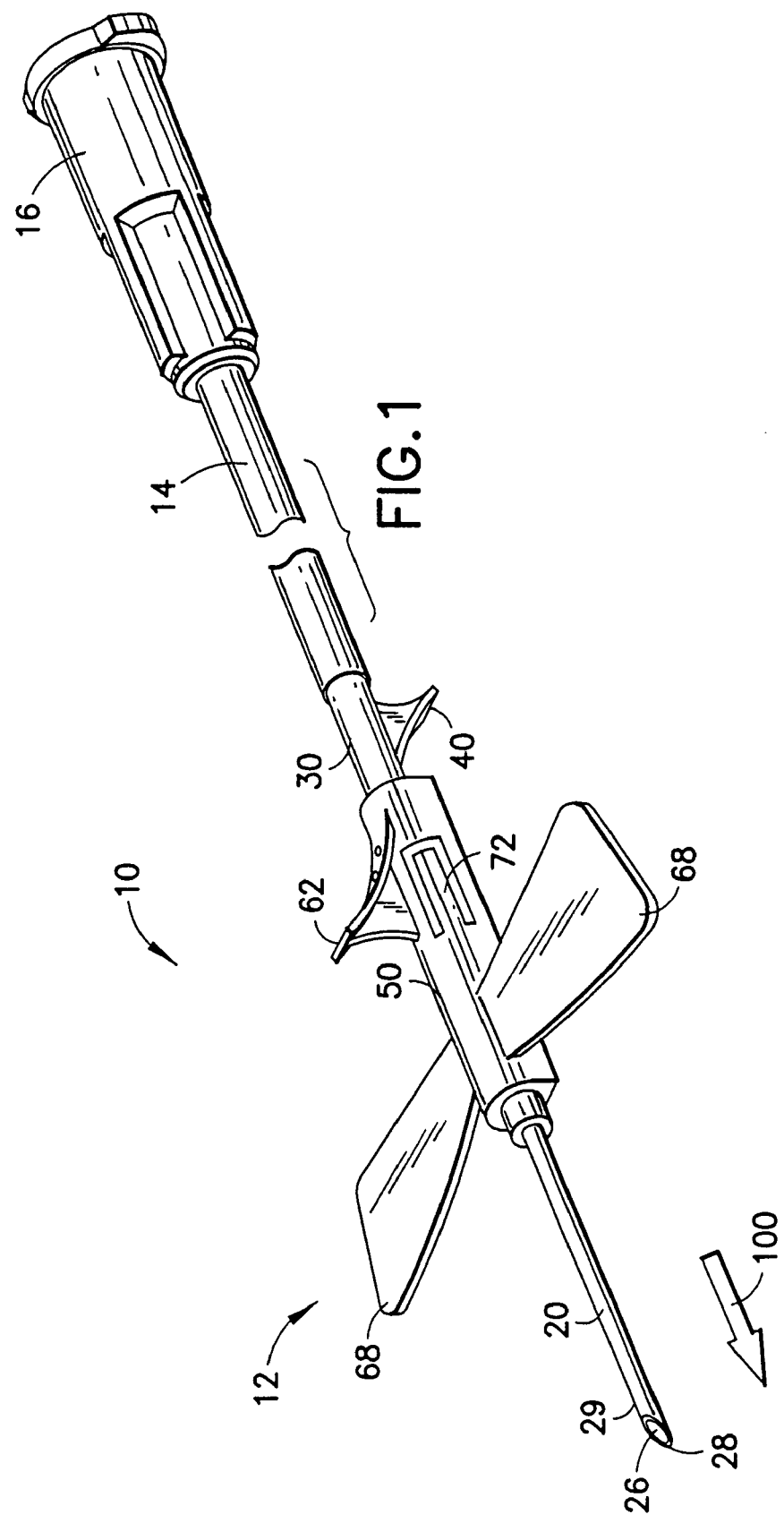
FIG. 1 is a perspective view of a blood collection set in accordance with the present invention.

Referring to the drawings in which like reference characters refer to like parts throughout the several views thereof, FIG. 1 illustrates a blood collection set 10 in accordance with the present invention and the related features. The present invention is generally described in terms of a blood collection set, and encompasses such a blood collection set as well as a shieldable needle assembly for use in such a blood collection set.

As shown in FIG. 1, blood collection set 10 includes a shieldable needle device 12, a flexible tube 14 extending from needle device 12 and a fixture 16 mounted to flexible tube 14. Shieldable needle device 12 of blood collection set 10 is shown in detail in FIGS. 2–9, and includes a needle cannula 20, a hub 30 and an outer shield 50. Fixture 16 is connectable to a receptacle (not shown) for use in blood collection procedures, as is known in the art.

Needle cannula 20 includes a proximal end 22 and an opposing distal end 24, with lumen 26 extending through needle cannula 20 from proximal end 22 to distal end 24. Distal end 24 of needle cannula 20 is beveled to define a sharp puncture tip 28, such as an intravenous puncture tip. Puncture tip 28 is provided for insertion into a patient's blood vessel, such as a vein, and is therefore designed to provide ease of insertion and minimal discomfort during venipuncture. A removable protective cover (not shown) may be positioned over distal end 24 of needle cannula 20 for protection from puncture tip 28 prior to use of blood collection set 10.

Figure 2:
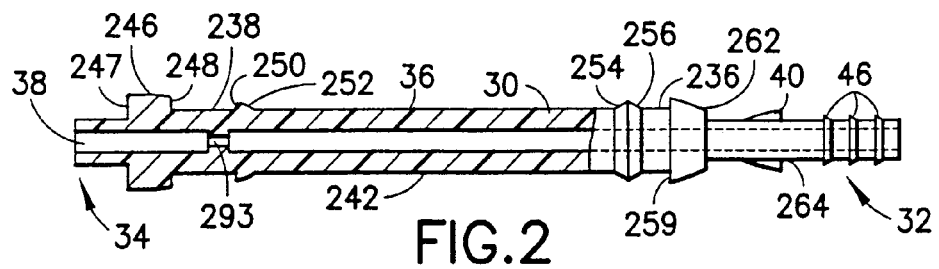
FIG. 2 is a top plan view of a hub adapted for receiving a needle cannula.
Figure 3:
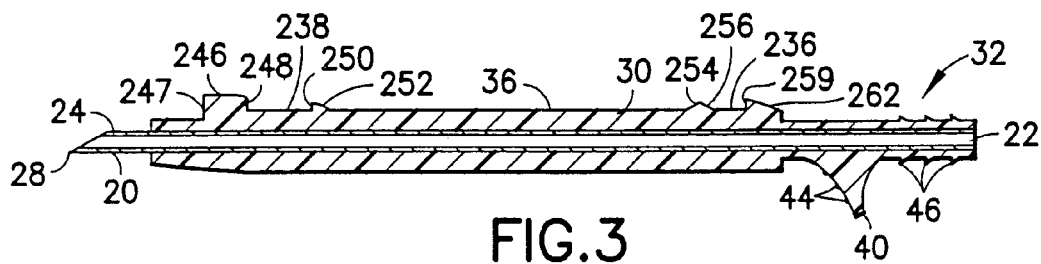
FIG. 3 is a side plan view of a hub including a needle cannula.
Figure 4:
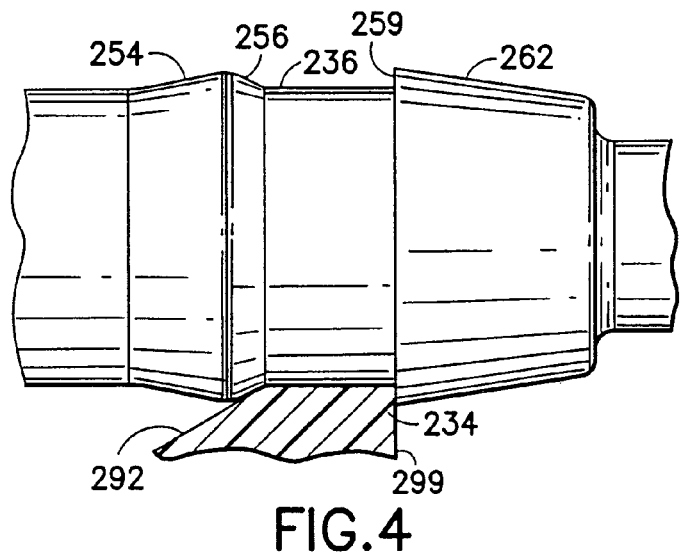
FIG. 4 is a side view of the second groove section of the hub shown in FIG. 2.
Figure 5:
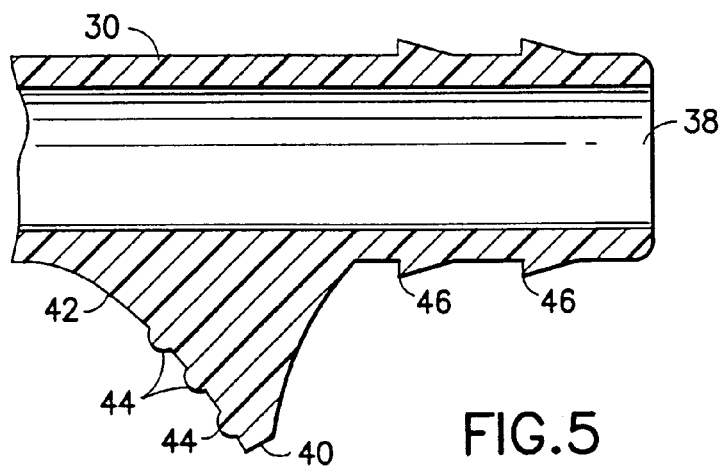
FIG. 5 is a side view of the proximal end of the hub shown in FIG. 2.

Needle assembly 12 further includes hub 30. Hub 30 is a unitary structure, desirably molded from a thermoplastic material. Hub 30 is a generally elongated tubular body having a proximal end 32, a distal end 34, an outer surface 36 and an internal passageway 38 extending therethrough from proximal end 32 to distal end 34. Needle cannula 20 is positioned within and is supported by internal passageway 38 of hub 30, with distal end 24 of needle cannula 20 extending from distal end 34 of hub 30. Desirably, needle cannula 20 and hub 30 are separate parts which are fixedly attached and secured through an appropriate medical grade adhesive or the like. As shown in FIG. 2, hub 30 may include a restriction 293 adjacent distal end 34 thereof, against which proximal end 22 of needle cannula 20 may abut. Alternatively, as shown in FIG. 3, needle cannula 20 may extend within the entire length of hub 30 to the proximal end 32 of hub 30.

Proximal end 32 of hub 30 is adapted for connection with a flexible tube 14 of blood collection set 10. Hub 30 desirably includes ribs 46 extending circumferentially about outer surface 36 at proximal end 32 of hub 30, for coupling with flexible tube 14.

Hub 30 further includes a first tab 40 extending outwardly from outer surface 36 at a location adjacent proximal end 32 of hub 30, and at a position distal to ribs 46. More particularly, first tab 40 extends from outer surface 36 of hub 30 at a position in front of the connection between hub 30 and flexible tube 14. In this manner, flexible tab 40 is accessible to a user's finger when needle device 12 is assembled with first tube 14 in blood collection set 10.

Desirably, first tab 40 extends from outer surface 36 at a bottom portion of hub 30 adjacent proximal end 32 of hub 30. Moreover, first tab 40 desirably extends in a direction toward flexible tube 14. First tab 40 includes a ramped surface 42 having protrusions 44 thereon, for providing frictional engagement with a user's finger.

Needle assembly 12 further includes hollow outer shield 50. Outer shield 50 includes a housing 52. Housing 52 is a unitary structure, desirably molded from a thermoplastic material, including a proximal end 54, a distal end 56 and an internal passageway 58 extending between proximal end 54 and distal end 56. The inner wall of housing 52 defines an internal surface 60 therethrough.

Outer shield 50 further includes a second tab 62 extending outwardly from a top portion of housing 52 near proximal end 54 of outer shield 50. Second tab 62 extends outwardly from outer shield 50 in a direction toward distal end 56 of outer shield 50. Second tab 62 includes a ramped surface 64 having protrusions 66 thereon for providing frictional engagement with a user's thumb.

Outer shield 50 co-axially surrounds distal end 34 of hub 30. In such a manner, proximal end 32 of hub 30 extends beyond proximal end 54 of outer shield 50 such that first tab 40 of hub 30 extends beyond proximal end 54 of outer shield 50. Moreover, internal surface 60 of outer shield 50 is in cooperating engagement with outer surface 36 of hub 30. Outer shield 50 is movable between a retracted position in which first tab 40 is exposed from proximal end 54 of outer shield 50 and puncture tip 28 is exposed from distal end 56 of outer shield 50, and an extended position in which puncture tip 28 and distal end 24 of needle cannula 20 are covered by outer shield 50.

First tab 40 and second tab 62 are configured such that opposing forces applied against first tab 40 and second tab 62 cause outer shield 50 to move toward distal end 24 of needle cannula 20 in a direction of arrow 100 from the retracted position to the extended position. Protrusions 44 and 66 on first tab 40 and second tab 62, respectively, provide frictional engagement with the user's finger and thumb, respectively, to facilitate moving outer shield 50 from the retracted position to the extended position.

Outer shield 50 may further include a pair of stabilizers in the form of wings 68 extending laterally from outer shield 50 at opposing sides thereof, providing blood collection set 10 as a butterfly-type wing assembly. Wings 68 assist in positioning and placing needle device 12 and blood collection set 10 during a blood collection procedure and are adapted to lie flat against the surface of a patient's skin during the blood collection procedure. As such, wings 68 may be constructed of a flexible material such that at least one, and desirably both, of wings 68 can be bent toward each other and brought together between the fingers of the user to assist in positioning and placing needle device 12 during venipuncture.

Housing 52 of outer shield 50 may also include a cutaway portion 70 extending through at least one side of housing 52, and desirably, extending through both sides of housing 52 at opposing lateral sides. Cutaway portion 70 defines a flexible finger 72, which is adapted for radial outward flexing during movement of outer shield 50 from the retracted position to the extended position, thereby permitting sliding engagement of outer shield 50 with respect to hub 30 about the cooperating surfaces thereof.

In particularly desirable embodiments, outer surface 36 of hub 30 and internal surface 60 of outer shield 50 include a plurality of corresponding grooves and ramped surfaces for providing cooperating axial movement therebetween in a predetermined manner. For example, as seen in FIGS. 2–6, outer surface 35 of hub 30 includes a front shoulder 246 of relatively large diameter. The front shoulder 246 is defined by a front face 247 and a rear abutment face 248. Directly behind the front shoulder 246 is a first groove 238 which is defined on one side by the abutment face 248 and on its other side by the termination (rear abutment face) 250 of a ramped surface 252. The ramped surface 252 starts with a diameter smaller than that of the front shoulder 246 and ramps downward away from the first groove 238. Ramp 252 terminates in a long valley 242 defined by outer surface 36 of hub 30. The valley 242 has a relatively constant diameter which is preferably substantially equal to the diameter of the first groove 238. The valley ends in a ramp 254 which increases in diameter as it extends away from distal end 34 and towards proximal end 32 of hub 30. Ramp 254 is followed by ramp 256 which ramps down to a second groove 236. Second groove 236 is preferably of a diameter slightly larger than the diameter of valley 242, and terminates in a rear abutment surface 259. Surface 259 is also the terminating surface of a rear ramp 262, which ends at portion 264 extending along proximal end 32 of hub 30. First tab 40 and ribs 46 extend from hub 30 at portion 264 extending along proximal end 32 of hub 30.

As is best seen in FIG. 3, hub 30 may be non-cylindrical such that it will not rotate inside of outer shield 50. With such a non-cylindrical shape, front shoulder 246, and ramps 252, 254, 256, and 262 do not appear on the bottom of outer surface 36 of hub 30. Thus, it should be appreciated that when "diameter" dimensions are provided, the term "diameter" is used in a broad sense to indicate relative cross-sectional dimensions.

Figure 9:
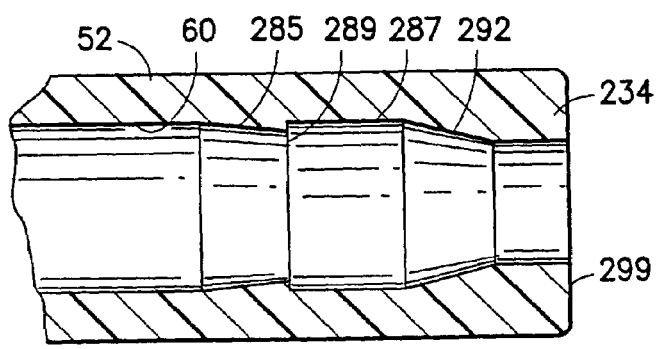
FIG. 9 is an enlarged plan view of the proximal end of the outer shield shown in FIG. 7.
Figure 7:
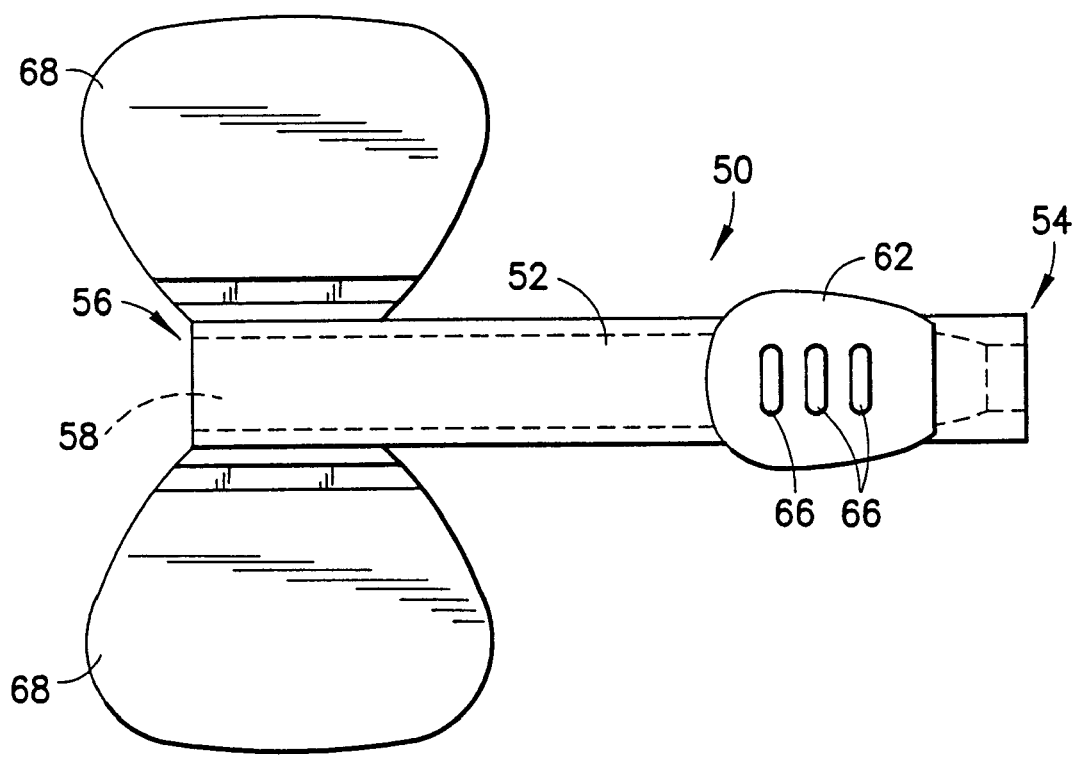
FIG. 7 is a plan view of a winged outer shield in accordance with the present invention.
Figure 8:
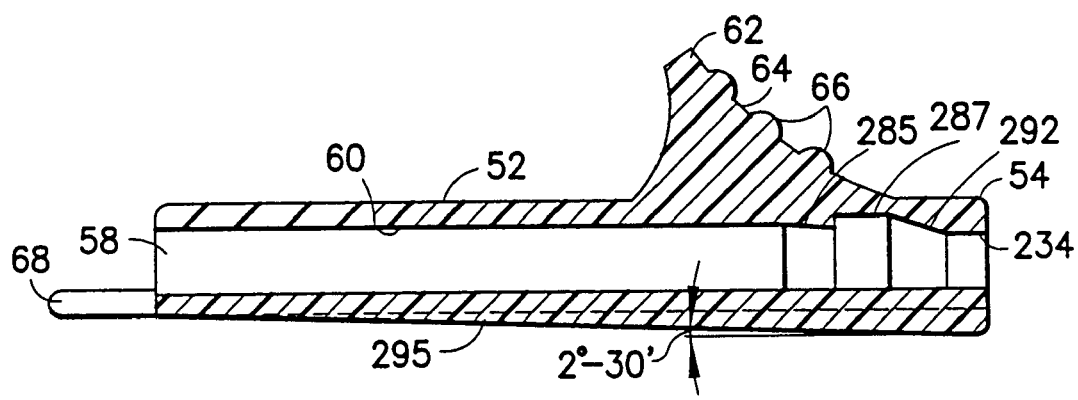
FIG. 8 is a side plan view of the outer shield shown in FIG. 7.

Turning to FIGS. 7–9, details of the outer shield 50 in one particular embodiment are shown. Housing 52 of outer shield 50 may be. nearly semicircular in cross-sectional shape, with a flat bottom surface 295. Flat bottom surface 295 is preferably a tapered surface (as seen in FIG. 8), with the thickness of the bottom increasing according to a two and one half degree slope as it extends away from distal end 56 of outer shield 50. As a result, when hub 50 and needle cannula 20 are positioned within outer shield 50, needle cannula 20 assumes a downward angle preferably of about two and one half degrees, and is more easily and comfortably inserted into the vein of the patient.

Internal surface 60 of housing 52 is of a diameter slightly larger than the outer diameter of front shoulder 246 of hub 30. However, towards proximal end 54, the inner surface of housing 52 is arranged with two ramps 285 and 292, although, if desired, ramp 285 may be replaced with a non-ramped protrusion. As seen in enlarged detail in FIG. 9, ramp 285 provides housing 52 with a decreasing inner diameter as it extends toward proximal end 54 of outer shield 50. Ramp 285 terminates in an abutment face 289 which is followed by a flat surface 287 having an inner diameter approximately equal to the outer diameter of shoulder 246 of hub 30. Flat surface 287 ends with ramp 292 which also has a decreasing inner diameter as it extends toward proximal end 54 of outer shield 50. The inner diameter at the end of ramp 292, however, is of significantly smaller diameter than that of ramp 285. Internal surface 60 of outer shield 50 terminates in a flat protrusion 234 of significantly smaller diameter than the diameter of the front shoulder 246, with rear surface 299 provided at proximal end 54 of housing 52.

Blood collection set 10 can be packaged substantially in the condition shown in FIG. 1. In particular, blood collection set 10 is provided with needle device 12 assembled and including flexible tube 14 extending from needle device 12 and connected to fixture 16. Prior to use, blood collection set 10 is removed from its package. After removing blood collection set 10 from its package, it can be assembled with other appropriate medical equipment for use. Fixture 16 then may be connected to an appropriate receptacle, such as a non-patient needle assembly and a needle holder, for providing fluid communication with lumen 26 through needle cannula 20.

To prepare for use of blood collection set 10, the user grasps blood collection set 10 at needle device 12 and removes the protective cover (not shown) to expose puncture tip 28 of needle cannula 20. The medical practitioner can then urge puncture tip 28 at distal end 24 of needle cannula 20 into a targeted blood vessel of a patient. During such positioning, at least one of wings 68 can be bent inwardly toward the other with the user's fingers to facilitate positioning and placing of needle device 12. Upon completion of the procedure, such as when all desired samples have been drawn, needle cannula 20 is withdrawn from the patient. After removal of needle cannula 20 from the patient, activation of the safety feature of needle device 12 is accomplished.

Figure 10:
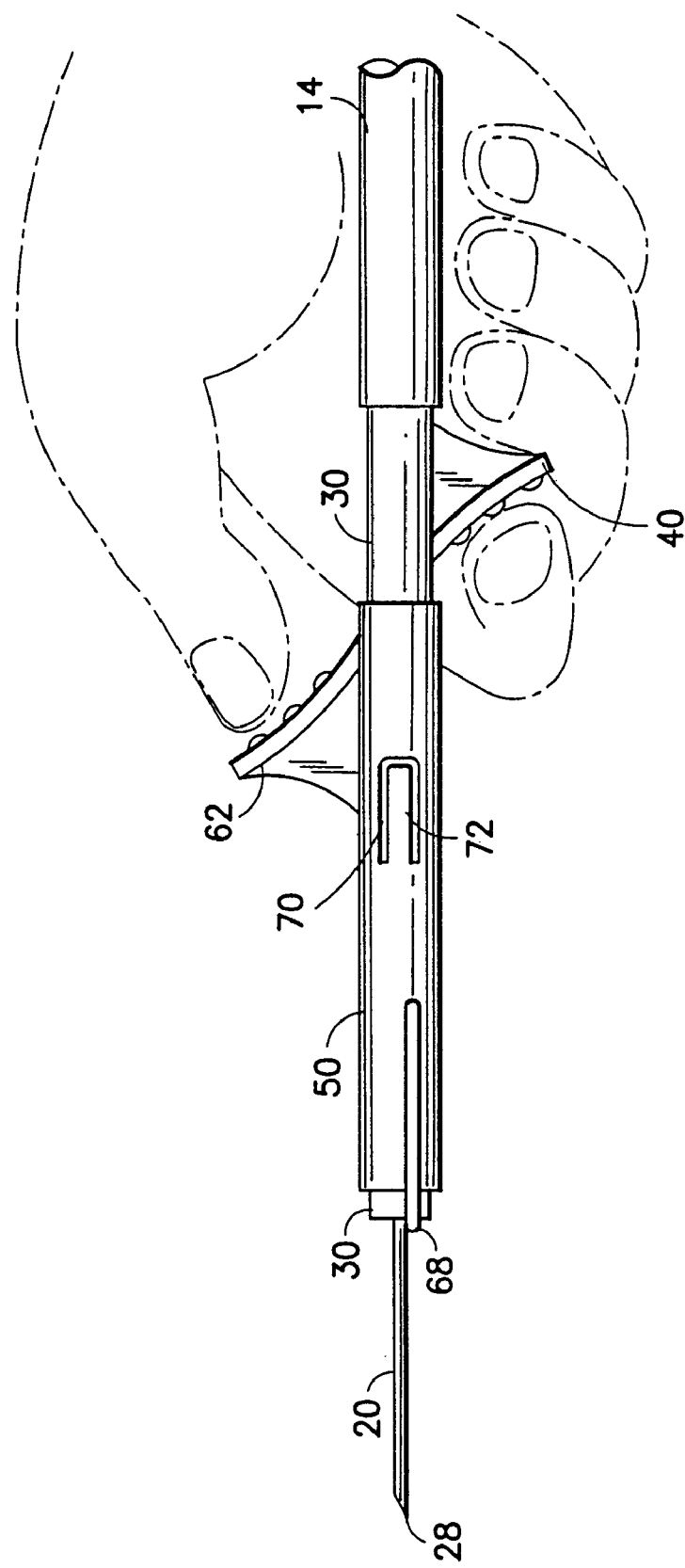
FIG. 10 is a side plan view of the blood collection set shown in FIG. 1 showing the outer shield in a retracted position.
Figure 11:
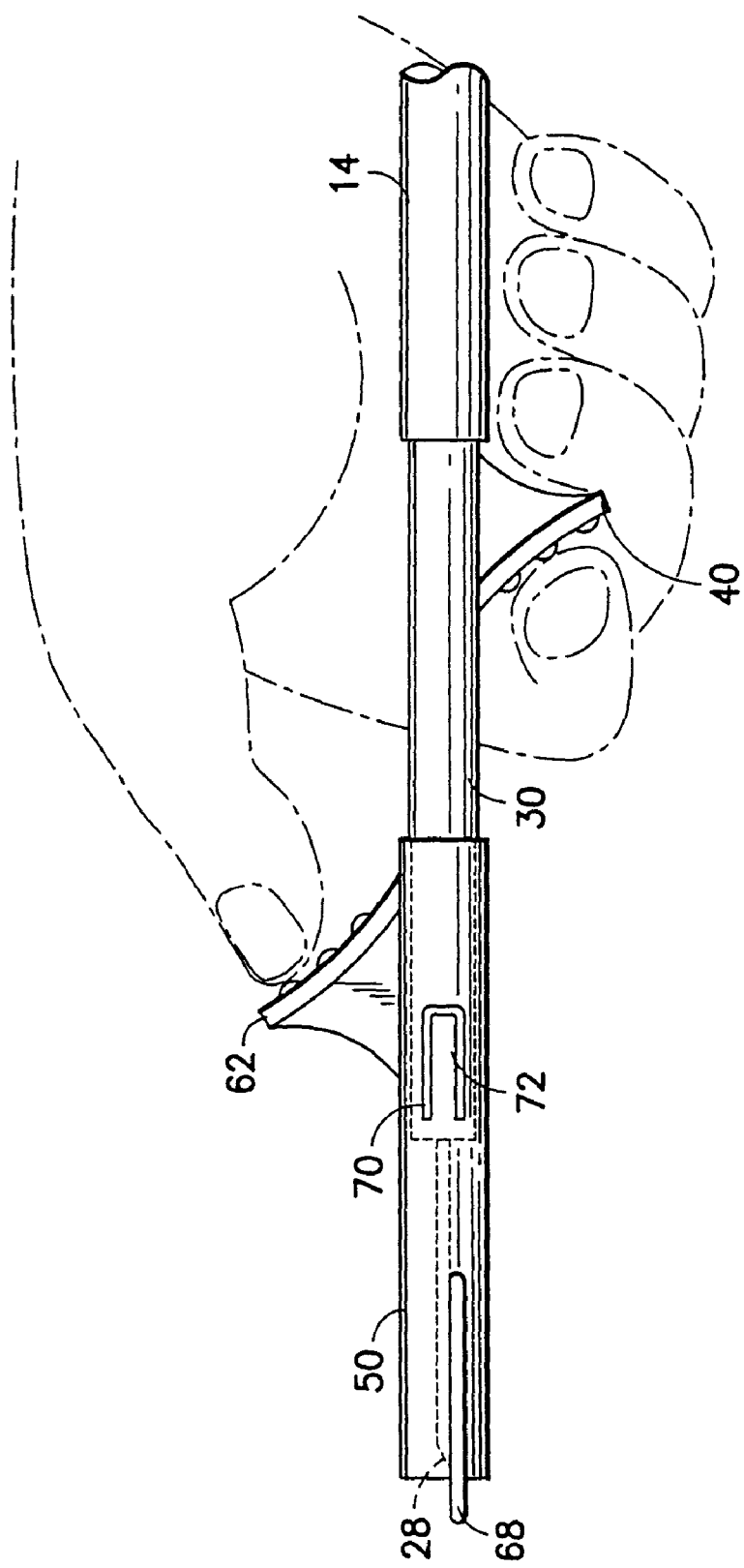
FIG. 11 is a side plan view of the blood collection set shown in FIG. 1 showing the outer shield in an extended position.

In particular, as shown in FIG. 10, the user grasps needle device 12 in one hand, with the user's thumb engaging first tab 40 and one of the user's forefingers engaging second tab 62. Opposed forces are exerted on first tab 40 and second tab 62 through the user's thumb and forefinger. Such opposing force causes outer shield 50 to move in the direction of arrow 100 from the retracted position to the extended position. Hence, puncture tip 28 of needle cannula 20 is safely shielded by outer shield 50 in the extended position as shown in FIG. 11. Blood collection set 10 may then be appropriately discarded.

Figure 6:
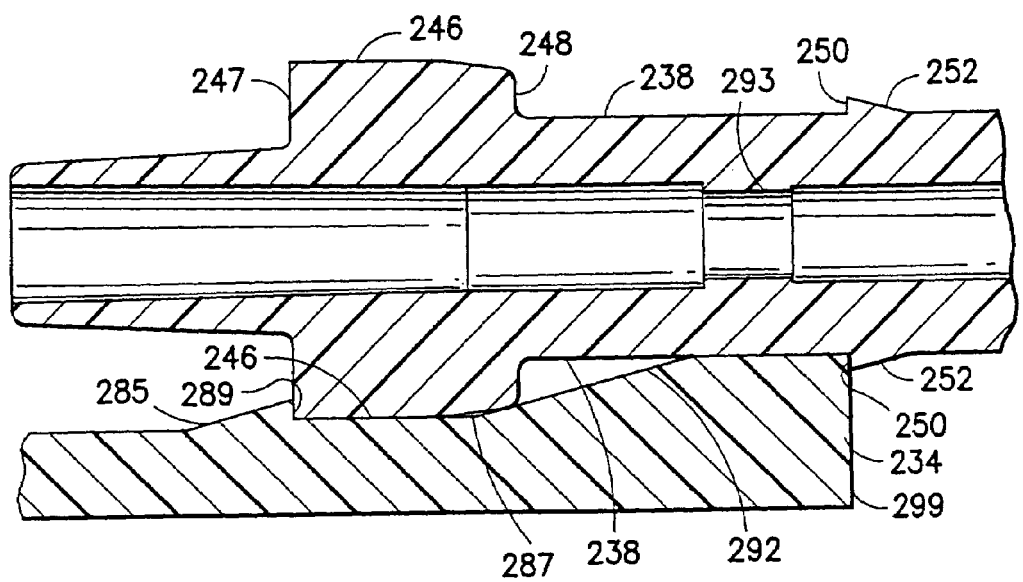
FIG. 6 is a side view of the first groove section at the distal end of the hub shown in FIG. 2.

In embodiments where outer surface 36 of hub 30 and internal surface 60 of outer shield 50 include a plurality of corresponding grooves and surfaces for cooperating engagement as described hereinabove, an initial force is required to overcome resistance of protrusion 234 sliding over ramp 256. In order to assist in such movement, flexible fingers 72 may flex radially outwardly from housing 52 of outer shield 50, thereby decreasing the resistance and permitting axial movement of outer shield 50 along hub 30. Once protrusion 234 slides over ramp 256, little force is needed to continue sliding outer shield 50 over valley 242 of hub 30. Additional resistance is encountered when ramp 252 of hub 30 encounters ramp 285 of housing 52, as well as when ramp 285 encounters front shoulder 246. With the application of differential force on first and second tabs 40 and 62, respectively, the design of needle device 12 including the cooperating surface assists in proper movement between the retracted position and the extended position. In particular, radial flexing of flexible fingers 72, the ramped nature of ramp 285 and the rounding of the edge of shoulder 246, permit ramp 285 to be slid over front shoulder 246 until it snaps over front shoulder 246 with abutment face 289 of outer shield 50 in contact with abutment surface 247 of front shoulder 246 of hub 30. At the same time, protrusion 234 sits in first groove 238 with rear surface 299 of outer shield 50 abutting abutment surface 250 of hub 30, and front shoulder 246 contacts surface 287. In this locked position, puncture tip 28 of needle cannula 20 is shielded entirely and securely by outer shield 50. Two locking interactions are established (abutment face 289 against shoulder 246, and rear surface 299 against surface 250) as seen in FIG. 6 to prevent return movement of outer shield 50 to the retracted position and reexposing of needle cannula 20, while the relative sizes of protrusion 234 and shoulder 246 prevent any possibility of outer shield 50 being pulled forward off of hub 30.

While the needle assembly of the present invention has been described in terms of one embodiment for use in connection with a blood collection system, it is further contemplated that the needle assembly could be used with other medical procedures, such as in conjunction with a conventional intravenous infusion set, which are well-known in the art for use with needle assemblies.

While the present invention is satisfied by embodiments in many different forms, there are shown in the drawings and described herein in detail, the preferred embodiments of the invention, with the understanding that the present disclosure is to be considered as exemplary of the principles of the invention and is not intended to limit the invention to the embodiments illustrated. Various other embodiments will be apparent to and readily made by those skilled in the art without departing from the scope and spirit of the invention. The scope of the invention will be measured by the appended claims and their equivalents.

What is claimed is:

1. A needle assembly, comprising:
   a needle cannula having a proximal end and a distal end with a puncture tip;
   a hub comprising an elongated tubular body having an outer surface, a proximal end, a distal end and a passageway extending through said hub, said distal end of said hub supporting said needle cannula, said hub further comprising a first tab extending outwardly from said proximal end of said tubular body; and
   a hollow outer shield comprising a housing having a proximal end, a distal end, a passageway extending from said proximal end to said distal end, and a second tab extending outwardly from said housing, said outer shield co-axially surrounding said distal end of said tubular body of said hub and including an inner surface in cooperating engagement with said outer surface of said tubular body of said hub, said outer shield movable between a retracted position in which said first tab extending from said tubular body is exposed from said proximal end of said outer shield and said puncture tip of said needle cannula is exposed from said distal end of said shield, and an extended position in which said outer shield covers said puncture tip of said needle cannula,
   wherein said first tab and said second tab are configured such that opposing forces applied against said first tab and said second tab cause said outer shield to move toward said distal end of said needle cannula from said retracted position to said extended position,
   such that said outer shield is locked in said extended position to prevent reexposure of said puncture tip of said needle cannula.

2. A needle assembly as in claim 1, wherein said first tab extends from a bottom portion of said hub and said second tab extends from a top portion of said housing of said outer shield.

3. A needle assembly as in claim 1, wherein said outer shield includes a pair of wing members extending laterally from opposing sides of said housing.

4. A needle assembly as in claim 1, wherein said outer surface of said hub includes a series of grooves and ramps and said inner surface of said outer shield cooperates with said outer surface of said hub, said grooves and ramps providing frictional engagement between said outer shield and said hub.

5. A needle assembly as in claim 4, wherein said housing of said outer shield includes at least one cutaway portion extending through said housing and defining a flexible finger, said at least one flexible finger adapted for outwardly flexing during movement of said outer shield from said retracted position to said extended position.

6. A needle assembly as in claim 1, wherein said proximal end of said hub is adapted for connection to a flexible tube of a blood collection set.

7. A needle assembly as in claim 1, wherein said first and said second tabs include protrusions for frictional engagement with a user's finger and thumb, respectively.

8. A shieldable blood collection set comprising:
   a fixture for connecting the blood collection set to a receptacle;
   a flexible tube having opposed first and second ends, said first end of said flexible tube being connected to said fixture;
   a hub including an elongated tubular body having an outer surface, a proximal end, a distal end and a passageway extending through said hub, said proximal end of said hub mounted to said second end of said flexible tube, said hub further including a first tab extending outwardly from said tubular body at said proximal end of said hub for engagement with a user's finger;
   a needle cannula extending from said distal end of said hub, said needle cannula including a proximal end and a distal end having a puncture tip; and
   a hollow outer shield comprising a housing having a proximal end, a distal end and a passageway extending therethrough, said outer shield co-axially surrounding said distal end of said tubular body of said hub such that said first tab of said hub is exposed from said proximal end of said outer shield, said outer shield adapted for movement between a retracted position in which said puncture tip of said needle cannula is exposed from said distal end of said shield, and an extended position in which said outer shield covers said puncture tip of said needle cannula, said housing of said outer shield having an inner surface in cooperating engagement with said outer surface of said hub and a second tab extending outwardly from said housing for engagement with a user's thumb;

wherein said first tab and said second tab are configured such that opposing forces applied against said first tab and said second tab cause said outer shield to move toward said distal end of said needle cannula, from said retracted position to said extended position, such that said outer shield is locked in said extended position to prevent reexposure of said puncture tip of said needle cannula.

9. A blood collection set as in claim 8, wherein said first tab includes a ramped surface extending outwardly from said tubular body of said hub at said proximal end of said hub in a direction toward said flexible tube.

10. A blood collection set as in claim 8, wherein said second tab includes a ramped surface extending outwardly from said housing of said outer shield at said proximal end of said outer shield in a direction toward said distal end of said outer shield.

11. A blood collection set as in claim 8, wherein at least one of said first tab and said second tab includes protrusions on a surface of said tab for providing a frictional engagement with a user.

12. A blood collection set as in claim 8, wherein said first tab extends from a bottom portion of said hub and said second tab extends from a top portion of said housing of said outer shield.

13. A blood collection set as in claim 8, wherein said outer shield includes a pair of wing members extending laterally from opposing sides of said housing.

14. A blood collection set as in claim 8, wherein said outer surface of said hub includes a series of grooves and ramps and said inner surface of said outer shield cooperates with said outer surface of said hub, said grooves and ramps providing frictional engagement between said outer shield and said hub.

15. A blood collection set as in claim 14, wherein said housing of said outer shield includes at least one cutaway portion extending through said housing and defining a flexible finger, said at least one flexible finger adapted for outwardly flexing during movement of said outer shield from said retracted position to said extended position.

* * * * *